(12) United States Patent
Coon et al.

(10) Patent No.: US 8,530,831 B1
(45) Date of Patent: Sep. 10, 2013

(54) PROBABILITY-BASED MASS SPECTROMETRY DATA ACQUISITION

(75) Inventors: Joshua Coon, Middleton, WI (US); Douglas Phanstiel, Palo Alto, CA (US); Graeme McAlister, Cambridge, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/418,972

(22) Filed: Mar. 13, 2012

(51) Int. Cl.
*G01N 33/00* (2006.01)

(52) U.S. Cl.
USPC ........... 250/282; 250/281; 250/283; 250/286; 250/287; 250/288

(58) Field of Classification Search
USPC .................................................. 250/281–300
See application file for complete search history.

(56) References Cited

U.S. PATENT DOCUMENTS

| | | | |
|---|---|---|---|
| 6,621,074 B1 | 9/2003 | Vestal | |
| 7,408,147 B2 | 8/2008 | Blick et al. | |
| 7,429,728 B2 | 9/2008 | Enke | |
| 7,473,892 B2 * | 1/2009 | Sano et al. | 250/281 |
| 7,498,568 B2 | 3/2009 | Overney et al. | |
| 7,548,818 B2 | 6/2009 | Kieser | |
| 7,555,393 B2 | 6/2009 | Sadygov et al. | |
| 7,638,763 B2 | 12/2009 | Guckenberger et al. | |
| 7,829,846 B2 | 11/2010 | Hashimoto et al. | |
| 7,884,324 B2 | 2/2011 | Blick et al. | |
| 7,982,070 B2 | 7/2011 | Smith et al. | |
| 7,982,181 B1 | 7/2011 | Senko | |
| 8,053,723 B2 | 11/2011 | Senko | |
| 8,274,059 B2 | 9/2012 | Blick et al. | |
| 8,278,115 B2 | 10/2012 | Coon et al. | |
| 2004/0121477 A1 | 6/2004 | Thompson et al. | |
| 2005/0267689 A1 | 12/2005 | Tsypin et al. | |
| 2007/0184455 A1 | 8/2007 | Arrowsmith et al. | |
| 2008/0044915 A1 * | 2/2008 | Hunt et al. | 436/89 |
| 2008/0203284 A1 | 8/2008 | Grothe | |
| 2010/0282957 A1 | 11/2010 | Wouters et al. | |
| 2010/0286927 A1 * | 11/2010 | Horn et al. | 702/19 |
| 2010/0330680 A1 | 12/2010 | Frey et al. | |
| 2011/0288779 A1 * | 11/2011 | Satulovsky | 702/19 |
| 2011/0297823 A1 | 12/2011 | Coon et al. | |
| 2011/0315868 A1 * | 12/2011 | Hirabayashi et al. | 250/282 |

(Continued)

FOREIGN PATENT DOCUMENTS

| | | |
|---|---|---|
| WO | 2007/109292 | 9/2007 |
| WO | 2009/073505 | 6/2009 |

OTHER PUBLICATIONS

International Search Report and Written Opinion for corresponding International Application No. PCT/US13/29300, Mailed May 23, 2013.

*Primary Examiner* — Michael Logie
(74) *Attorney, Agent, or Firm* — Lathrop & Gage LLP

(57) ABSTRACT

An algorithm-based system and method for tandem mass spectrometry data acquisition in which multiple precursor ion attributes, such as mass, intensity, mass-to-charge ratio and charge state, as well as results from previously performed mass spectrometry scans, are used to determine the likelihood of identification for each precursor ion. This information is then used to prioritize subsequent tandem mass spectrometry events, such as which precursor ions are to be fragmented and undergo further mass spectrometry analysis. By interrogating precursor ions in order of probability of successful identification, an increase in identified proteins and peptides is achieved.

26 Claims, 5 Drawing Sheets

(56) References Cited

U.S. PATENT DOCUMENTS

2012/0022230 A1 1/2012 Smith et al.
2012/0049058 A1 3/2012 Grothe
2012/0091330 A1 4/2012 Coon et al.
2012/0261568 A1 10/2012 Coon et al.
2013/0078728 A1 3/2013 Li et al.
2013/0084645 A1 4/2013 Coon et al.

* cited by examiner

US 8,530,831 B1

PROBABILITY-BASED MASS SPECTROMETRY DATA ACQUISITION

STATEMENT REGARDING FEDERALLY SPONSORED RESEARCH OR DEVELOPMENT

This invention was made with government support under GM080148 awarded by the National Institutes of Health. The government has certain rights in the invention.

BACKGROUND OF THE INVENTION

This invention is in the field of mass spectrometry, more particularly to methods of data acquisition in tandem mass spectrometry.

The ability to identify proteins and determine their chemical structures has become central to the life sciences. The amino acid sequence of proteins provides a link between proteins and their coding genes via the genetic code, and, in principle, a link between cell physiology and genetics. The identification of proteins provides a window into complex cellular regulatory networks.

Mass spectrometry (MS) is commonly used to provide information related to protein composition and peptide sequence. As efforts shift from sequencing the genome to understanding and identifying expressed genes and protein function, it is increasingly important that analytical tools be developed for providing reliable and rapid protein sequencing. Such protein sequence information can be used in proteomic databases and for identifying, understanding and using sequence information in a wide range of applications from fundamental research to medical treatment.

Ion trap mass spectrometers are among the most widely used platforms for molecular analysis—spanning natural products, to pharmaceuticals, to biologics such as proteins. Most mass spectrometer-based experiments begin with the isolation of a group of compounds from a set of samples through some sort of extraction technique, e.g., proteins from tissues, cell lysates, or fluids followed by proteolytic digestion of those proteins into peptides. Frequently, but not necessarily, the mass spectrometers are coupled with some form of separations, e.g., electrophoretic or chromatographic. Over the course of just a few hours, mass spectral instruments can autonomously interrogate tens of thousands of molecular species.

In tandem mass spectrometry (MS/MS or $MS^2$), multiple rounds of mass spectrometry analysis are performed. For example, samples containing a mixture of proteins and peptides can be ionized and the resulting precursor ions separated according to their mass-to-charge ratio. Selected precursor ions can then be fragmented and further analyzed according to the mass-to-charge ratio of the fragments.

Technical developments in chromatography and MS instrumentation have made two types or protein sequencing methods popular: (1) the bottom-up approach and (2) the top-down approach. For the bottom-up approach, a protein-containing sample is digested with a proteolytic enzyme resulting in a complex mixture of peptides. Next, the digested sample is chromatographically separated (in one or multiple dimensions) and introduced to an electrospray ionization (ESI) source on the mass spectrometer. The ESI source converts condensed phase ions, eluting from the HPLC column, to multiply-protonated molecules (cations) in the gas-phase—a requirement for MS analysis. The mass spectrometer first records the mass/charge (m/z) of each peptide ion and then selects the peptide ions individually to obtain sequence information via MS/MS. In a typical shotgun proteomics experiment a cell lysate, containing as many as several thousand proteins, is analyzed. In the top-down method intact proteins are ionized and directly sampled by the mass spectrometer and then fragmented during MS/MS analysis.

Liquid chromatography coupled to MS/MS is arguably the most common and most effective method for global identification of peptides and proteins. The m/z peaks corresponding to the precursor ions are plotted with respect to intensity on a mass spectrum, and represent fragments that can be further analyzed to identify peptides and proteins of interest. For complex mixtures, however, not all precursor ions can be selected for further analysis within a given elution window. Furthermore, many of the peaks and corresponding precursor ions do not lead to successful identification of the protein or peptide. The most common solution to this has been to select peaks in order of decreasing intensity. The precursor ions having the least intense peaks are then excluded from consideration for a set amount of time.

However, selecting precursor ions solely by intensity of their initial MS peaks does not always result in the selection of precursor ions most likely to lead to successful identification of the protein or peptide. Selecting precursor ions using another characteristic, such as their mass-to-charge ratio, may be more advantageous depending on the sample and MS/MS conditions, but similarly may not result in the selection of precursor ions most likely to lead to successful identification.

Moreover, selection of the precursor ions may occur when the attributes of some precursor ions are not ideal (e.g., they exhibit low intensity or are observed in the presence of other more abundant precursors with similar m/z ratios) thus precluding their identification. Almost all modern LC-MS/MS methods employ some version of "dynamic exclusion". Dynamic exclusion ensures that once a precursor ion is selected for fragmentation and subsequent $MS^2$ analysis, it is excluded from further $MS^2$ selection for a fixed, user-defined amount of time (typically 30-90 seconds). The rationale is that there are many precursor ions to interrogate and it is inefficient to repeat $MS^2$ analysis on the same precursor ions multiple times. However, these methods are based on some basic assumptions that are very often not true: (1) that the likelihood of a successful identification is constant for the entire period of time that the precursor ion is observed in $MS^1$ scans; and (2) that there are always new precursor ions to select for fragmentation and $MS^2$ analysis.

In many cases, a precursor ion can be selected for $MS^2$ analysis when its $MS^1$ intensity is very low or when it could be observed in the presence of a much more abundant precursor a mere 0.3 Daltons away. The probability that the precursor ion will be successfully identified from the $MS^2$ scan during this time period may be very low. However, twenty seconds later it might be much more intense and the neighboring precursor ion might not be present any more. In such cases, it may be worth performing another $MS^2$ analysis on this precursor ion. This is especially true if the duty cycle on the mass spectrometer is extremely fast and has already selected all of the peaks in the $MS^1$ window for $MS^2$ analysis, which can be observed with modern mass spectrometers. By excluding these precursor ions from consideration via dynamic exclusion there is no opportunity to reselect them for $MS^2$ analysis when their attributes are more suited for identification.

What is needed is an improved method of data acquisition that enables the selection of precursor ions more likely to lead to successful identification, including precursor ions which may normally be excluded from further analysis.

SUMMARY OF THE INVENTION

The present invention provides a method for MS/MS data acquisition in which multiple precursor ion attributes, such as intensity, mass-to-charge ratio and charge state, are used to determine the likelihood of identification for each precursor ion. The present invention also provides a further method where the likelihood of identifying a precursor ion for the first time in that data set or experimental set is determined. This information is then used to prioritize subsequent MS/MS events. By interrogating precursor ions in order of probability of successful identification or successful novel identification rather than in order of decreasing peak intensity, an increase in identified proteins and peptides is achieved.

In one embodiment of the present invention, a test sample containing a mixture of compounds, preferably a mixture of proteins or peptides, is analyzed using MS/MS. In one embodiment, one or more compounds within the mixture are labeled with isobaric tags. The compounds within the mixture are ionized and separated according to their mass-to-charge ratio, thereby generating precursor ions. The precursor ions are detected and analyzed to generate information related to the physical properties of the ions, which can include but are not limited to attributes such as mass, intensity, mass-to-charge ratio and charge state. One or more precursor ions are selected for further analysis and are fragmented. The fragmented ions are separated according to their mass-to-charge ratio and detected to generate information related to physical properties of the fragment ions, which again can include, but are not limited to, mass, intensity, mass-to-charge ratio and charge state. Particularly with protein and peptide mixtures, the fragment ion information is used to identify and characterize the compounds in the test sample.

The precursor ions selected for fragmentation and further MS analysis are prioritized based on the probability of that precursor ion being successfully identified and/or the desirability of further analyzing that precursor ion over other precursor ions. The probability of identification for the precursor ions is calculated using the attributes of the precursor ions generated from the first MS scan. In a further embodiment, the probability of successfully identifying each precursor ion is calculated using two or more attributes, three or more attributes, four or more attributes, or five or more attributes. Precursor ions having a higher calculated probability of identification are prioritized for the subsequent MS analysis over precursor ions having a lower calculated probability of identification.

As used herein, "prioritized" and "prioritizing" refers to ranking precursor ions wherein precursor ions having a higher ranking or a higher prioritization are preferentially analyzed in subsequent steps over precursor ions having lower prioritization. For example, in some instances precursor ions having a higher calculated probability of identification are prioritized so that they are fragmented before precursor ions having a lower calculated probability of identification. In other instances, this means that precursor ions having a higher calculated probability of identification undergo further MS analysis while precursor ions having a lower calculated probability of identification are excluded from further analysis. Alternatively, all or most precursor ions undergo fragmentation and further MS analysis but increased system resources are allocated to the detection and analysis of precursor ions having a higher calculated probability of identification. In a further embodiment, an algorithm allows for sequential analysis of the different precursor ions based on their probability of being identified and also allows for precursor ions to be resampled in order to confirm the identity and minimize errors.

A further embodiment of the present invention involves training or calibrating the mass spectrometer to recognize attributes, fragments, conditions or parameters that result in an increased probability of identification. For example, a well characterized sample (such as a yeast lysate) is used to train or calibrate the mass spectrometer. This training step establishes which precursor ion attributes and the degrees to which each attribute are most effective in determining which precursor ions are most likely to be identified. After the general parameters of the different attributes have been established, the test sample is run through the mass spectrometer and an algorithm selects the precursor ions most likely to be identified.

Tandem mass spectrometry systems useful for the present invention include, but are not limited to, the following types of instruments: triple quadrupole (QqQ), time-of-flight (TOF), quadrupole time-of-flight (QqTOF), fourier transform ion cyclotron resonance (FTICR), four-sector (BEBE), orbitrap, and ion trap mass spectrometers. In addition, the methodology of the present invention is compatible with current mass spectrometers with little to no increase in analysis time or additional hardware. The present invention can be implemented on existing mass spectrometers as a software update or incorporated into the software bundled with new hardware. The methods of the present invention would also be particularly useful on slower machines for prioritization and on faster machines for re-identification (confirmation).

Preferably, the calculation of probability of identification and prioritization of precursor ions for MS/MS analysis are performed in real-time. In the present invention, "real-time" refers to the ability to perform subsequent actions (such as a $MS^2$ scan) based on data obtained during mass spectrometric operation (such as the $MS^1$ scan) or from subsequent analysis or database searching of data generated by the mass spectrometer. For example, scan rates of the methods disclosed herein can be on the order of 1 scan per second, sufficiently fast to permit results of that scan to influence or effect a change in how subsequent MS scans are conducted.

One embodiment of the present invention provides a method of analyzing an analyte using tandem mass spectrometry, wherein the method comprises: (a) providing an analyte; (b) generating a distribution of precursor ions from the analyte; (c) analyzing two or more precursor attributes of at least a portion of the distribution of precursor ions, and using the precursor attributes to calculate probabilities of identification for at least a portion of the precursor ions; (d) prioritizing said precursor ions according to which precursor ions have a greater calculated probability of identification, thereby generating a set of prioritized precursor ions; (e) fragmenting one or more prioritized precursor ions and generating a distribution of fragment ions; and (g) measuring one or more attributes of at least a portion of the distribution of the fragment ions, thereby generating product ion mass spectrometry data. In a further embodiment, the probabilities of identification are calculated ion using two or more attributes, three or more attributes, four or more attributes, or five or more attributes. In an embodiment, precursor ions are fragmented in order of prioritization. Optionally, precursor ions having higher calculated probability of identification are fragmented before precursor ions having lower calculated probability of identification. Alternatively, a plurality of precursor ions are fragmented wherein increased detection or analyzing resources are assigned to fragment ions having higher calculated probability of identification. Preferably, the analyte is a mixture of proteins and peptides where one or more proteins or peptides are optionally isobarically labeled.

In a further embodiment, the present invention uses attributes from the current MS scans as well as attributes from previous $MS^1$ and $MS^2$ scans (preferably from the same LC-MS/MS experiment) to determine the probability that a particular precursor ion has already been successfully identified and the probability that this precursor ion could be successfully identified if selected in the current scan cycle. These estimations determine the combined probability that the precursor ion has not been previously identified but would be identified if selected now. In this embodiment, precursor ion selection is prioritized based on the probability that a precursor ion will be successfully identified for the first time in a data set or experimental set.

This further embodiment provides a method of analyzing an analyte using tandem mass spectrometry, wherein the method comprises: (a) providing an analyte; (b) generating a distribution of precursor ions from the analyte; (c) analyzing two or more precursor attributes of at least a portion of the distribution of precursor ions, and using the precursor attributes to calculate probabilities of identification for at least a portion of the precursor ions; (d) determining whether the one or more precursor ions have been previously selected for mass spectrometry analysis, and calculating the probabilities that the one or more precursor ions have not been identified in previous mass spectrometry analysis; and (e) using the calculated probabilities of identification and the calculated probabilities that the one or more precursor ions have not been identified in previous mass spectrometry analysis to generate probabilities of novel identification for the one or more precursor ions. The precursor ions are then prioritized according to which precursor ions have a greater probability of novel identification, thereby generating a set of prioritized precursor ions. The one or more prioritized precursor ions are fragmented to generate a distribution of fragment ions; and one or more attributes of at least a portion of the distribution of the fragment ions are measured, thereby generating product ion mass spectrometry data. In an embodiment, precursor ions are fragmented in order of prioritization. In a further embodiment, the probabilities of identification are calculated ion using two or more attributes, three or more attributes, four or more attributes, or five or more attributes As used herein, the term "probability of novel identification" refers to the probability that the precursor ion will be successfully identified for the first time with respect to the present set of LC-MS/MS experiments, or a database containing MS/MS identification data. Optionally, precursor ions having a higher probability of novel identification are fragmented before precursor ions having lower probability of novel identification. Alternatively, a plurality of precursor ions are fragmented wherein increased detection or analyzing resources are assigned to fragment ions having a higher probability of novel identification. Preferably, the analyte is a mixture of proteins and peptides.

The probability of identification and probability of novel identification for the one or more of the precursor ions can be calculated using statistical methods known in the art. In one embodiment, the probability of identification and/or probability of novel identification are calculated using generalized linear models, decisions trees, or support vector machines. In a further embodiment, the probability of identification and/or probability of novel identification are calculated using a computer based algorithm. In an embodiment, the algorithm is a computational based process which compares and evaluates the experimental spectra of the precursor ions to a known database of sequences, features, sequence tags or databases.

In further embodiments, the two or more analyzed attributes of the precursor ions are selected from the group including, but not limited to, mass, signal intensity, mass-to-charge ratio, charge state, signal to noise ratio, composition, and whether precursor ions are present with a similar mass-to-charge ratio. Similarly, the one or more measured attributes of the fragment ions are selected, independently from the precursor ion attributes, from the group including, but not limited to, mass, signal intensity, mass-to-charge ratio, charge state, signal to noise ratio, composition, and presence or absence of other precursor ions with a similar mass-to-charge ratio. As used herein, similar mass-to-charge ratio refers to ions having a mass-to-charge ratio within 10% of one another, within 5% of one another, within 2% of one another, or within 1% of one another. In a further embodiment, the probability of identification for each precursor ion is calculated using an algorithm which uses the two or more, three or more, four or more, or five or more precursor ion attributes. Preferably, the analyzing, calculating and fragmenting steps are performed in real-time.

Another embodiment of the present invention provides a method of analyzing an analyte using tandem mass spectrometry, wherein a training sample is used to help calculate the probability of identity. In this embodiment, the method comprises: (a) performing mass spectroscopy analysis on a training sample, thereby generating data values for a plurality of training attributes; (b) selecting two or more training attributes corresponding to said training sample, wherein said selected training attributes have data values corresponding to a higher probability of identification for said training sample than unselected training attributes; (c) providing an analyte; (d) generating a distribution of precursor ions from the analyte; (e) analyzing, in real-time, two or more precursor attributes of at least a portion of the distribution of precursor ions, wherein said precursor attributes correspond to the selected training attributes, and using the precursor attributes to calculate probabilities of identification for at least a portion of the precursor ions; (f) prioritizing, in real-time, said precursor ions according to which precursor ions have a greater calculated probability of identification, thereby generating a set of prioritized precursor ions; (g) fragmenting one or more prioritized precursor ions and generating a distribution of fragment ions; and (h) measuring one or more attributes of at least a portion of the distribution of the fragment ions, thereby generating product ion mass spectrometry data. Preferably, the analyte is a mixture of proteins and peptides. In an embodiment, precursor ions are fragmented in order of prioritization. In a further embodiment, the probabilities of identification are calculated ion using two or more attributes, three or more attributes, four or more attributes, or five or more attributes The training sample can be a single known compound, a well characterized mixture of compounds, or even an unknown mixture of compounds, and does not necessarily need to share the same characteristics (e.g. sample preparation method or species of origin) as the test samples to be analyzed later. For example, the training sample can be a cell lysate (such as a yeast lysate) where the exact protein composition is not known, or a mixture having a known composition of proteins and peptides. In one embodiment, the training sample can be selected beforehand in order to specifically determine which attributes correspond to a higher probability of identification. In another embodiment, the training sample is a previous test sample.

Where a known compound or mixture of compounds is used as the training sample, the identified compounds can be compared to the known identity of the training sample to evaluate which training attributes resulted in increased successful identification. Where the exact composition of the training sample is not known, subsequent evaluation of the mass spectrometry data can be used to determine if the MS/MS analysis of the training sample resulted in successful identifications or false identifications of the components. In either case, attributes which correlate with higher successful identifications of the training sample with less false identifications are preferentially selected for future experiments.

After acquiring data during a test run, several methods as known in the art can be used to determine which scans did and did not result in a positive identification. In one commonly used method, each spectrum is compared against a protein database and scored. Using standard techniques, peptide identifications are assigned and filtered to a fixed estimated (often 1%) false discovery rate. Each scan can then be categorized as successful or unsuccessful.

Using this data set which now consists of known predictive variables (attributes such as mass, charge, intensity, etc.) and known outcomes (successful or unsuccessful identification) it is possible to apply any one of many available statistical methods (e.g. generalized linear models, decision trees, support vector machines) to create a model that can predict the probability of identification given a specific combination of predictive variables. For many of these statistical models, no prior knowledge is required regarding how the particular variable impacts the success or failure of identification.

The training attributes useful in the present invention can include, but are not limited to, mass, signal intensity, mass-to-charge ratio, charge state, signal to noise ratio, composition, and whether other precursor ions are present with a similar mass-to-charge ratio. The two or more precursor ion attributes used to generate the precursor ion mass spectrometry data of the target analyte will be selected from the training attributes which correlate to successful identification of the training sample. The one or more measured attributes of the fragment ions during the $MS^2$ stage of the test sample are similarly selected from the group comprising mass, signal intensity, mass-to-charge ratio and charge state but are selected independently from the training attributes and precursor ion attributes. In a further embodiment, an algorithm is use to select the two or more precursor attributes and to calculate the probability of identification for each precursor ion.

An embodiment of the invention further comprises providing an analyte, where the analyte is a mixture, and labeling one or more compounds, molecules, peptides or proteins within the mixture with one or more isobaric tagging reagents.

Another embodiment of the present invention provides a tandem mass spectrometer system for analyzing an analyte, the system comprising: a) an ion source for generating ions from the analyte; b) first ion separation optics in communication with the ion source for separating ions according to their mass-to-charge ratios; c) a first ion detector in communication with the first ion separation optics for detecting ions separated according to their mass-to-charge ratios; d) ion fragmentation optics in communication with the first ion separation optics for generating fragment ions; e) second ion separation optics in communication with the ion fragmentation optics for separating ions according to their mass-to-charge ratios; f) a second ion detector in communication with the second ion separation optics for detecting ions separated according to their mass-to-charge ratios; and g) a controller operably connected to the first and second ion separation optics, the first and second ion detectors, and the ion fragmentation optics.

The controller controls the ion optics and detectors and is able to, in real-time, generate a distribution of precursor ions from the analyte, measure two or more attributes of at least a portion of the distribution of the precursor ions, fragment the precursor ions, create a distribution of fragment ions, and measure one or more attributes of at least a portion of the distribution of the fragment ions. Additionally, the controller can, in real-time, prioritize the fragmentation and/or measurement of fragment ions for precursor ions that have a higher calculated probability of identification or a higher probability of novel identification. In a further embodiment, the controller records attributes of precursor ions from prior samples and evaluates which attributes correlate to successful identification. The controller uses this information to calculate the probability of identification for the current precursor ions. In another embodiment, the evaluation of which attributes correlate to successful identification is done by a component other than the controller and this information is outputted to the controller. The controller then prioritizes the fragmentation and/or measurement of fragment ions based on which precursor ions have a higher calculated probability of identification.

DETAILED DESCRIPTION OF THE INVENTION

Definitions

Figure 1:
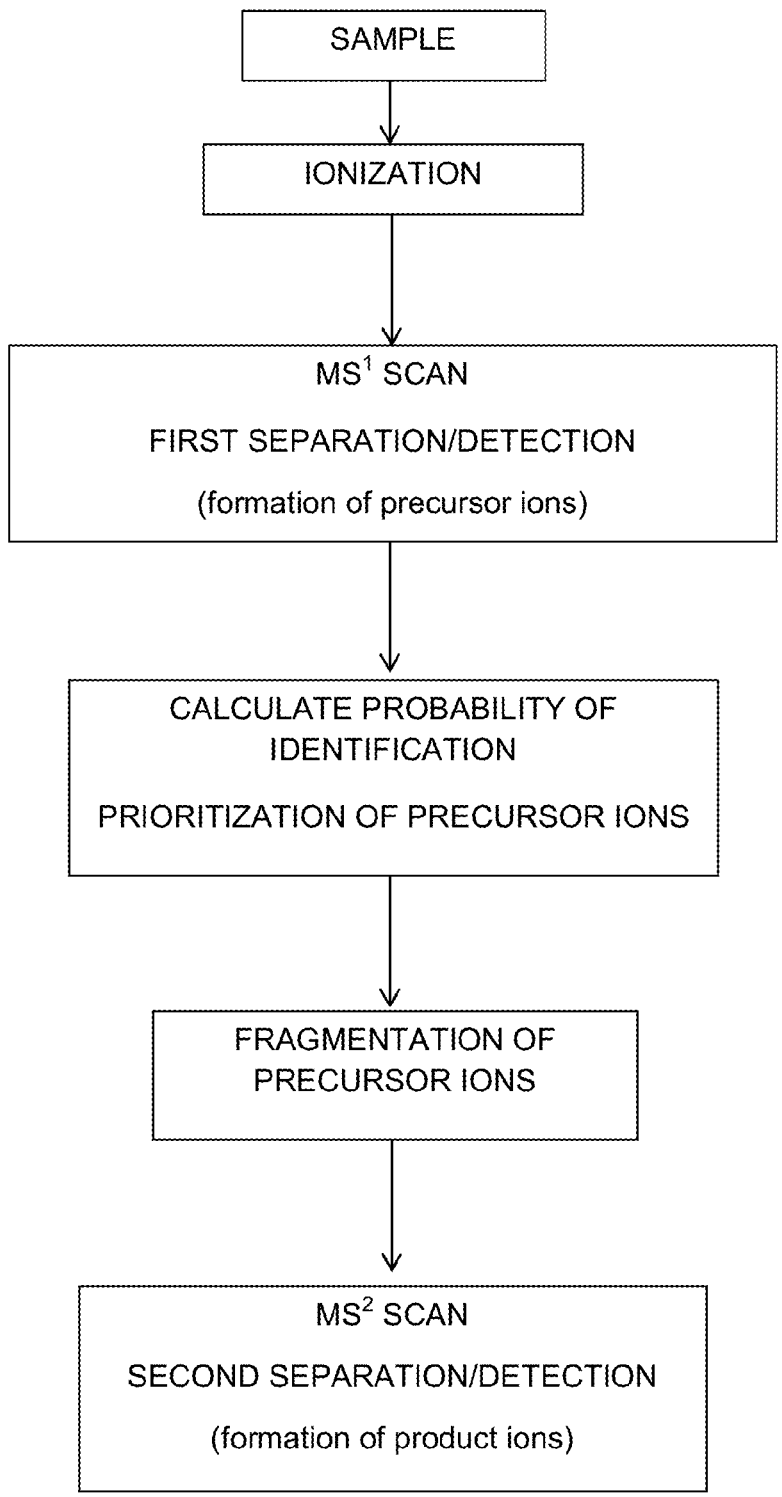
FIG. 1 provides a flow chart showing steps of a method of the present invention. The probability of identification for a set of precursor ions is calculated after a $MS^1$ scan. Based on the calculated probability of identification, the precursor ions are prioritized for the subsequent fragmentation step and $MS^2$ scan.

In general the terms and phrases used herein have their art-recognized meaning, which can be found by reference to standard texts, journal references and contexts known to those skilled in the art. The following definitions are provided to clarify their specific use in the context of the invention.

As used herein, the term "analyzing" refers to a process for determining a property of an analyte. Analyzing can determine, for example, physical properties of analytes, such as mass, mass-to-charge ratios, or substituent composition.

As used herein, the term "analyte" refers to a compound or composition which is the subject of an analysis. Analytes include, but are not limited to, proteins, peptides, small molecules, pharmaceutical compounds, oligonucleotides, sugars and mixtures thereof. In many embodiments described herein, the analyte is a mixture containing multiple proteins and peptides and the methods of the present invention are used to determine the identity of proteins and peptides in the mixture.

As used herein, the term "mass spectrometry" refers to an analytical technique for the determination of the elemental composition of an analyte. Mass spectrometric techniques are useful for elucidating the chemical structures of analytes, such as peptides and other chemical compounds. The mass spectrometry principle consists of ionizing analytes to generate charged species or species fragments and measurement of their mass-to-charge ratios. Conducting a mass spectrometric analysis of an analyte results in the generation of mass spectrometry data relating to the mass-to-charge ratios of the analyte and analyte fragments. Mass spectrometry data corresponding to analyte ion and analyte ion fragments is presented in mass-to-charge (m/z) units representing the mass-to-charge ratios of the analyte ions and/or analyte ion fragments.

As used herein, the term "mass-to-charge ratio" refers to the ratio of the mass of a species to the charge state of a species. The term "m/z unit" refers to a measure of the mass to charge ratio. The Thomson unit (abbreviated as Th) is an example of an m/z unit and is defined as the absolute value of the ratio of the mass of an ion (in Daltons) to the charge of the ion (with respect to the elemental charge).

In tandem mass spectrometry (also called MS/MS or $MS^2$), a second MS analysis is performed. Typically, analyte ions which have undergone a first MS analysis (often referred to as the $MS^1$ stage) are dissociated into fragment ions. The fragment ions are then analyzed (often referred to as the $MS^2$ stage), providing further information about the molecular structure of the precursor ion. A second mass analyzer is often required, hence the term 'tandem MS'. MS/MS/MS, also called $MS^3$ or sometimes $MS^n$, subjects the fragment ions themselves to further fragmentation steps. More fragmentation gives even more information about the molecular structure of the precursor ion, but at a cost of reduced sensitivity as well as increased analysis time. MS/MS/MS can typically only be performed on abundant peptides.

As used herein, the term "precursor ion" refers to an analyte ion formed during the first MS analysis. Similarly, the terms "product ion" or "secondary ions" refer to ions which are produced during a fragmentation process of a precursor ion.

As used herein, the term "mass spectrometer" refers to a device which creates ions from a sample, separates the ions according to mass, and detects the mass and abundance of the ions. Mass spectrometers include multistage mass spectrometers which fragment the mass-separated ions and separate the product ions by mass one or more times. Multistage mass spectrometers include tandem mass spectrometers which fragment the mass-separated ions and separate the product ions by mass once.

As used herein, the term "ion source" refers to a device component which produces ions from a sample. Examples of ion sources include, but are not limited to, electrospray ionization sources and matrix assisted laser desorption/ionization (MALDI) sources.

As used herein, the term "ion optic" refers to a device component which assists in the transport and manipulation of charged particles, for example ions, by the application of electric and/or magnetic fields. The electric or magnetic field can be static, alternating, or can contain both static and alternating components. Ion optical device components include, but are not limited to, ion deflectors which deflect ions, ion lenses which focus ions, and multipoles (such as quadruples) which confine ions to a specific space or trajectory. Ion optics include multipole RF device components which comprise multiple rods having both static and alternating electric and/ or magnetic fields.

As used herein, the term "controller" refers to a device component which can be programmed to control a device or system, as is well known in the art. Controllers can, for example, be programmed to control mass spectrometer systems as described herein. Controllers can be programmed, for example, to carry out ion manipulation and sample analysis methods as described herein on systems and devices as described herein and as otherwise known in the art.

The terms "peptide" and "polypeptide" are used synonymously in the present description, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides include, for example, polypeptides comprising 1 to 100 amino acid units, optionally for some embodiments 1 to 50 amino acid units and, optionally for some embodiments 1 to 20 amino acid units.

"Protein" refers to a molecule comprising multiple amino acids linked together via peptide bonds. The twenty amino acids genetically encoded in an organism's genome are the basic building blocks of proteins. Alternatively, the protein can be synthetically constructed or bioengineered. Each protein has a unique amino acid sequence, and so identification of a portion of a protein sequence can provide information as to protein identity. An amino acid may be chemically modified after expression by a mechanism referred to as "post-translational modification." For example, the amino-end of an amino acid is often acetylated, which makes the protein more resistant to degradation. Other examples include hydroxylation, carboxylation, methylation, oxidation and phosphorylation, among others. Although a protein may be of any length so long as the protein maintains biological activity, proteins are generally made up of more than about 50 amino acids.

"Fragmenting" refers to breakage of a polypeptide to generate charged species that can be detected by a mass spectrometer, thereby providing means for mass determination of the charged species. "Selectively fragmenting" refers to specifically breaking a polypeptide to ensure generation of a detectable and measurable amount of c- and z-type product ions. Other type of product ions may be generated, depending on the fragmentation means employed.

Ion fragmentation for peptide and protein sequence analysis, with RF 3D quadrupole ion traps (QIT), quadrupole time-of-flight (Qq-TOF), and RF linear multipole ion trap (QLT) instruments, is generally performed via collision-activated dissociation (CAD). In this process, peptides that are protonated more or less randomly on backbone amide nitrogen atoms are kinetically excited and undergo collisions with an inert gas such as helium or argon. During each collision, imparted translational energy is converted to vibrational energy that is then rapidly distributed throughout all covalent bonds (ca. psec timescale). Fragment ions are formed when the internal energy of the ion exceeds the activation barrier required for a particular bond cleavage. Fragmentation of protonated amide bonds affords a homologous series of complementary product ions of type b and y. Subtraction of the m/z values for the fragments within a given ion series that differ by a single amino acid, affords the mass, and thus the identity of the extra residue in the larger of the two fragments. The complete amino acid sequence of a peptide can be directly deduced (de novo interpretation) by extending this process to all homologous pairs of fragments within a particular ion series.

Electron transfer dissociation (ETD) is a more recent technology for peptide fragmentation. Rather than using collisions, ETD reacts the selected peptide cations with anions of fluoranthene (or other negatively charged small molecules). This reaction proceeds by transfer of an electron from the fluoranthene anion to the peptide (an ion/ion reaction). The added electron causes the peptide to break randomly between each amino acid. Once the peptide is fragmented the masses of each fragment are then recorded. Unlike CAD, ETD causes cleavage of a different backbone bond to produce c and z-type fragment ions, rather than the b and y-type fragments generated by CAD. ETD can be considered a derivative of electron capture dissociation (ECD) which uses free electrons rather than anions to induce the same fragmentation pathways.

EXAMPLES

In the following examples, numerous specific details of the devices, device components and methods of the present invention are set forth in order to provide a thorough explanation of the precise nature of the invention. It will be apparent, however, to those of skill in the art that the invention can be practiced without these specific details.

Example 1

Sample Preparation

*Saccharomyces cerevisiae* (Yeast) and human embryonic stem (ES) cells were grown, harvested, and then lysed by either French press (Yeast) or sonication (ES cells). Proteins reduced with dithiothreitol, alkylated with iodoacetamide, and digested with either Lys-C (yeast) or trypsin (ES cells) at 37 degrees Celsius overnight. Digested peptides were purified by solid phase extraction, dried to completion and resolubilized in mobile phase A (0.2% formic acid) prior to analysis.

Example 2

Mass Spectrometry

All mass spectrometry experiments were carried out on a hybrid linear ion trap-orbitrap mass spectrometer (Thermo Scientific). Samples were separated via reversed phase chromatography (Waters, nanoAcquity UPLC) and coupled directly to the mass spectrometer via a nano electrospray ion source. All $MS^1$ scans were detected in the orbitrap mass analyzer, which permitted real time determination of intensity, mass, and charge for each precursor. All $MS^2$ scans were detected in the linear ion trap mass analyzer. LC-MS/MS experiments were approximately 120 minutes long.

For training runs, each duty cycle consisted of one $MS^1$ scan followed by $MS^2$ (CAD) of the ten most intense precursors. Dynamic exclusion was employed in order to reduce the number of redundant $MS^2$ scans. To test the method, two types of analyses were performed: control and testing. The duty cycle of these experiments consisted of one $MS^1$ scan followed by ten $MS^2$ scans. For the control runs the $MS^2$ scans were prioritized in by intensity. For the testing runs the MS/MS scans were prioritized by probability of successful ID. Since the probability calculations require overhead time, the calculations for both control and testing runs were performed immediately following each $MS^1$ scan.

Example 3

Database Searching

In order to identify peptides, the COMPASS software suite was used. This software suite identifies peptides by comparing $MS^2$ spectra against a concatenated forward/reversed protein database (Saccharomyces Genome Database for yeast and Internal Protein Index for human). Results were ranked by expectation value and filtered to a 1% False Discovery Rate (FDR) based on the proportion of reversed to forward peptides identifications.

Example 4

Probability Estimations

Probabilities of identification were estimated by generalized linear models. Using the data from all three training runs, the data was searched using the COMPASS software suite which allowed every $MS^2$ scans to be assigned as either not identified or identified with a FDR of 1%. Using this data, generalized linear models were built separately for each precursor charge state (0 (unknown), 1, 2, 3, 4, 5, and $\geq 6$) using the following formula:

$$\mathrm{logit}(p) = A(\ln(I)) + Bm + Cm^2 + Dm^3 \quad \text{(equation 1)}$$

where I is the intensity of the precursor and m is the mass-to-charge ratio of the precursor. Using the R statistical environment, a generalized linear model was constructed that determined values for the coefficients A, B, C, and D. This was repeated for each charge state (0, 1, 2, 3, 4, 5, and $\geq 6$).

The control software of the onboard computer on the mass spectrometer was such that after ever $MS^1$ scan it would determine the intensity, mass, and charge of the 1000 most intense peaks. For each peak it would calculate the probability of successful identification using the following formula:

$$P = \frac{e^{\mathrm{logit}(p)}}{1 - e^{\mathrm{logit}(p)}} \quad \text{(equation 2)}$$

where P is the probability of successful identification and logit(p) is calculated as described in equation 1.

Example 5

Probability of Identification

Figure 3:
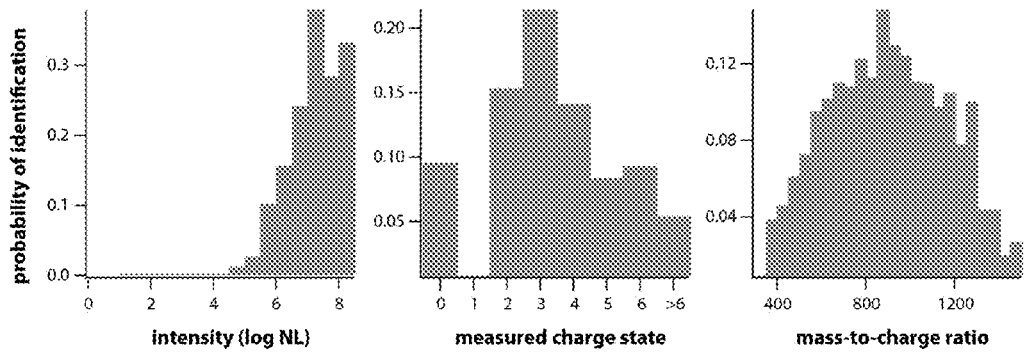
FIG. 3 shows the correlation between certain peak attributes, such as intensity, measured charge state, and mass-to-charge ratio, and the probability of identification for a set of peptides.

As shown in FIG. 3, different values for different peak attributes, such as intensity, measured charge state, and mass-to-charge ratio, can indicate a different probability of identification for a set of peptides. Rather than rely on a single attribute, such as peak intensity as is commonly done, the present invention takes into account multiple attributes to calculate the probability of a particular peak being successfully identified.

FIG. 1 provides a flow chart showing steps of MS/MS analysis in one method of the present invention. A sample is ionized and the resulting precursor ions undergo a first MS analysis (the $MS^1$ scan). Using the attributes of the precursor ions measured during the $MS^1$ stage, the probability of identification for one or more of the precursor ions is calculated. Based on the calculated probability of identification, the precursor ions are prioritized for the subsequent fragmentation step and $MS^2$ scan.

Figure 2:
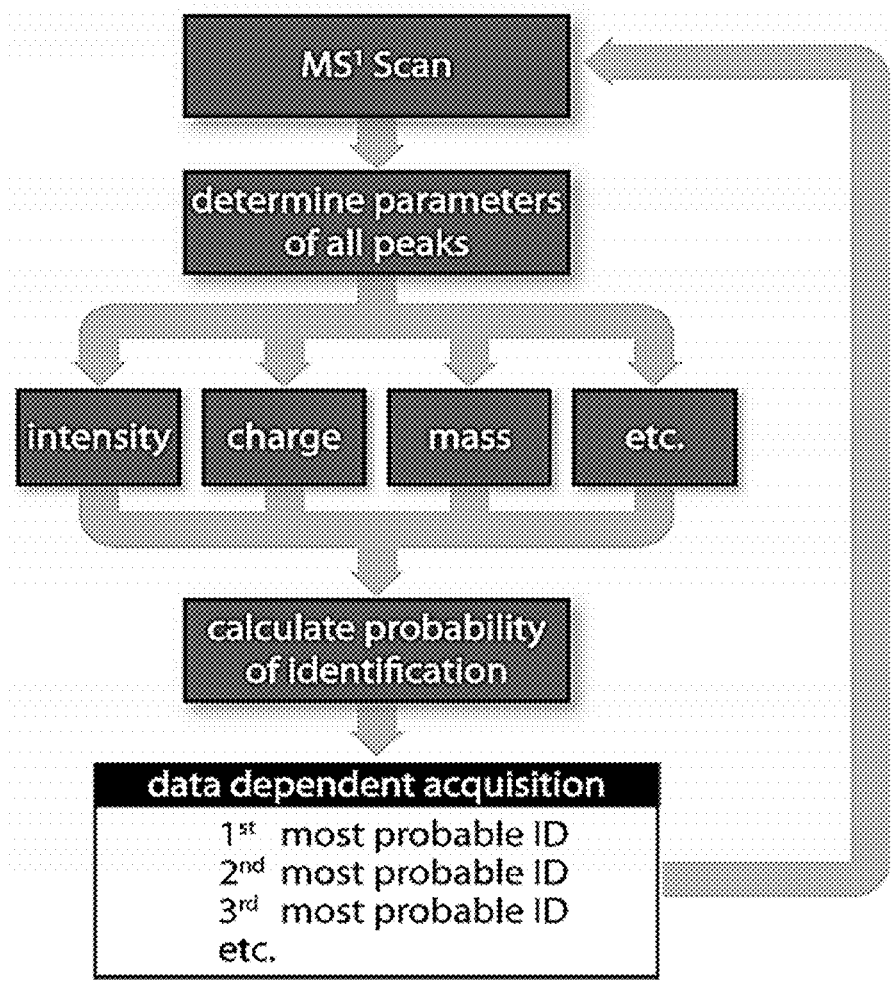
FIG. 2 provides a flow chart showing parameters used to calculate probability of identification in one embodiment of the invention. In addition to the parameters of peaks resulting from the $MS^1$ scan, results from previous scans and data acquisitions from the current LC-MS/MS experiment can also be used to affect subsequent scans and determine subsequent calculations of probability of identification.
Figure 4:
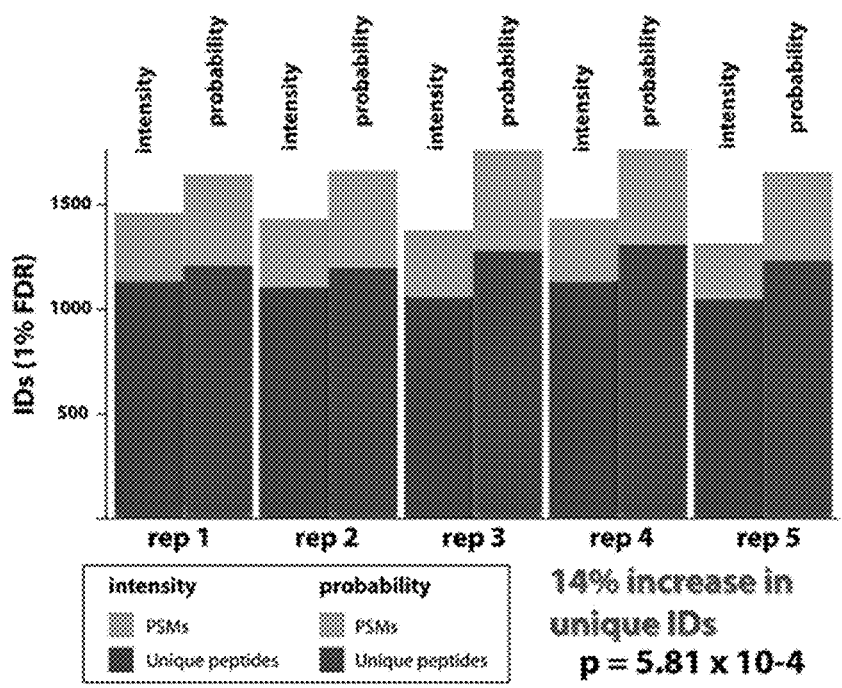
FIG. 4 shows results from one embodiment of the present invention in which training and testing was performed on the same sample. The model yeast proteins were digested with Lys-C and analyzed 3 times by LC-MS/MS. In order to test methods of the present invention, the same sample (yeast proteins that were digested with Lys-C) was analyzed by LC-MS/MS 10 times: 5 times using intensity to prioritize MS/MS events, and 5 times using probabilities as predicted by a generalized linear model to prioritize MS/MS events. The ten test runs were staggered and run in the order they are shown (from left to right).

As illustrated in FIG. 2, multiple attributes from the $MS^1$ scan can be used to calculate probability of identification for the precursor ions. Results from prior scans can then be evaluated and used to determine which attributes will lead to increased protein identification in subsequent scans. For example, a statistical model can be used to determine which attributes from prior scans correlate to successful identification. Based on this information, MS/MS events in subsequent scans will be prioritized. In one experiment, yeast proteins were digested with Lys-C and analyzed 3 times by LC-MS/MS. The same sample (yeast proteins that were digested with Lys-C) was then analyzed by LC-MS/MS 10 times: 5 times using intensity to prioritize MS/MS events, and 5 times using probabilities of identification as predicted by a generalized linear model to prioritize MS/MS events. The ten test runs were staggered and run in the order shown in FIG. 4. Using probabilities of identification to prioritize MS/MS events resulted in a 14% increase in successful protein identifications.

Figure 5:
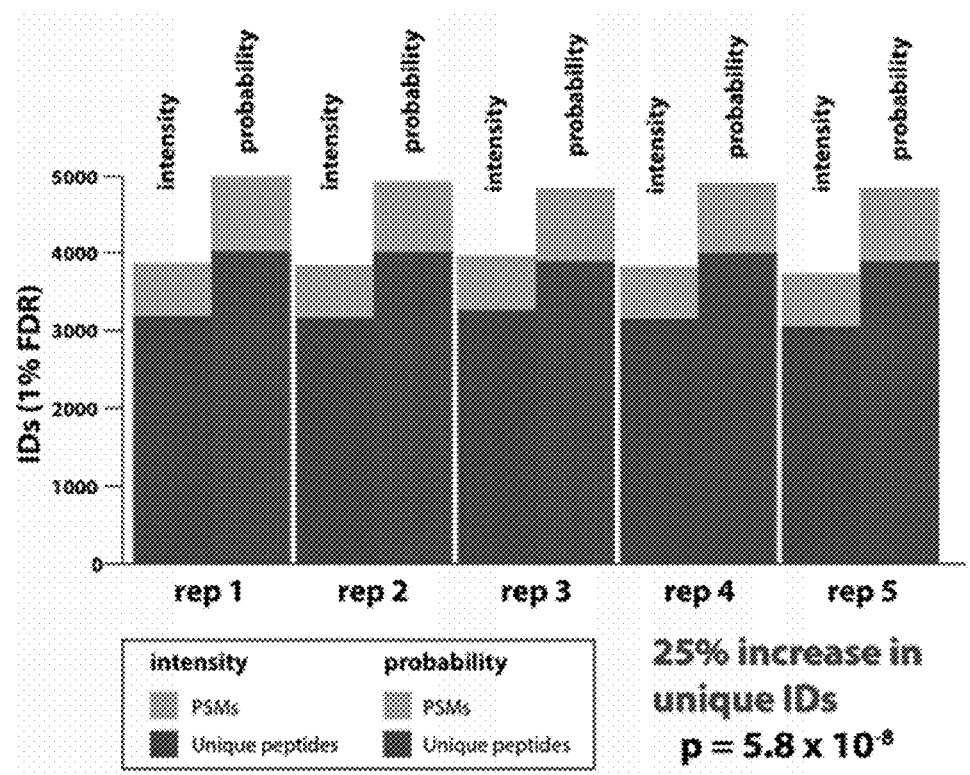
FIG. 5 shows results from one embodiment of the present invention in which training and testing was performed on different samples. Yeast proteins were digested with Lys-C and analyzed 3 times by LC-MS/MS. In order to test methods of the present invention, proteins harvested from human embryonic stem cells were digested with trypsin and analyzed by LC-MS/MS 10 times: 5 times using intensity to prioritize MS/MS events, and 5 times using probabilities as predicted by a generalized linear model to prioritize MS/MS events. The ten test runs were staggered and run in the order they are shown (from left to right).

A similar experiment was performed where the sample generating the initial mass spectrometry data was different than the test sample. Yeast proteins were digested with Lys-C and analyzed 3 times by LC-MS/MS. Data from these scans were used to determine which attributes correlated to an increased probability of identification and used to prioritize MS/MS events in subsequent test samples. Proteins harvested from human embryonic stem cells were digested with trypsin and analyzed by LC-MS/MS 10 times: 5 times using intensity to prioritize MS/MS events, and 5 times using probabilities as predicted by a generalized linear model to prioritize MS/MS events. The ten test runs were staggered and run in the order shown in FIG. 5. This particular experiment resulted in a 25% increase in successful protein identifications of the human tryptic digest.

Example 6

Probability of Novel Identification

If prioritization based upon the probability of a novel identification (i.e., identification of a previously unidentified compound in a particular data set or experimental set) is more desirable than being able to successfully identify compounds which have been previously identified, results from previous scans (such as from the same LC-MS/MS experiment) can also be used. In order to determine the probability of a novel identification, the current attributes of a precursor ion (such as mass, charge, intensity, etc.) are considered in conjunction with attributes exhibited by the precursor ion from previous MS scans. In this experiment three probabilities were calculated for each precursor: (1) the probability that the precursor ion has already been identified; (2) the probability that the precursor ion will be identified if selected for $MS^2$ in the current scan cycle; and (3) the probability that the precursor ion has not been previously identified but will be identified if selected now (see FIG. 6). Subsequent $MS^2$ events will be prioritized based on the probability that a previously unidentified compound will be identified with the current $MS^2$ analysis. It is important to note that in calculating the probability that a precursor ion has already been identified, both $MS^1$ and $MS^2$ attributes be used including, but not limited to, overall intensity, intensity in different m/z ranges, and charge states of peaks.

Figure 6:
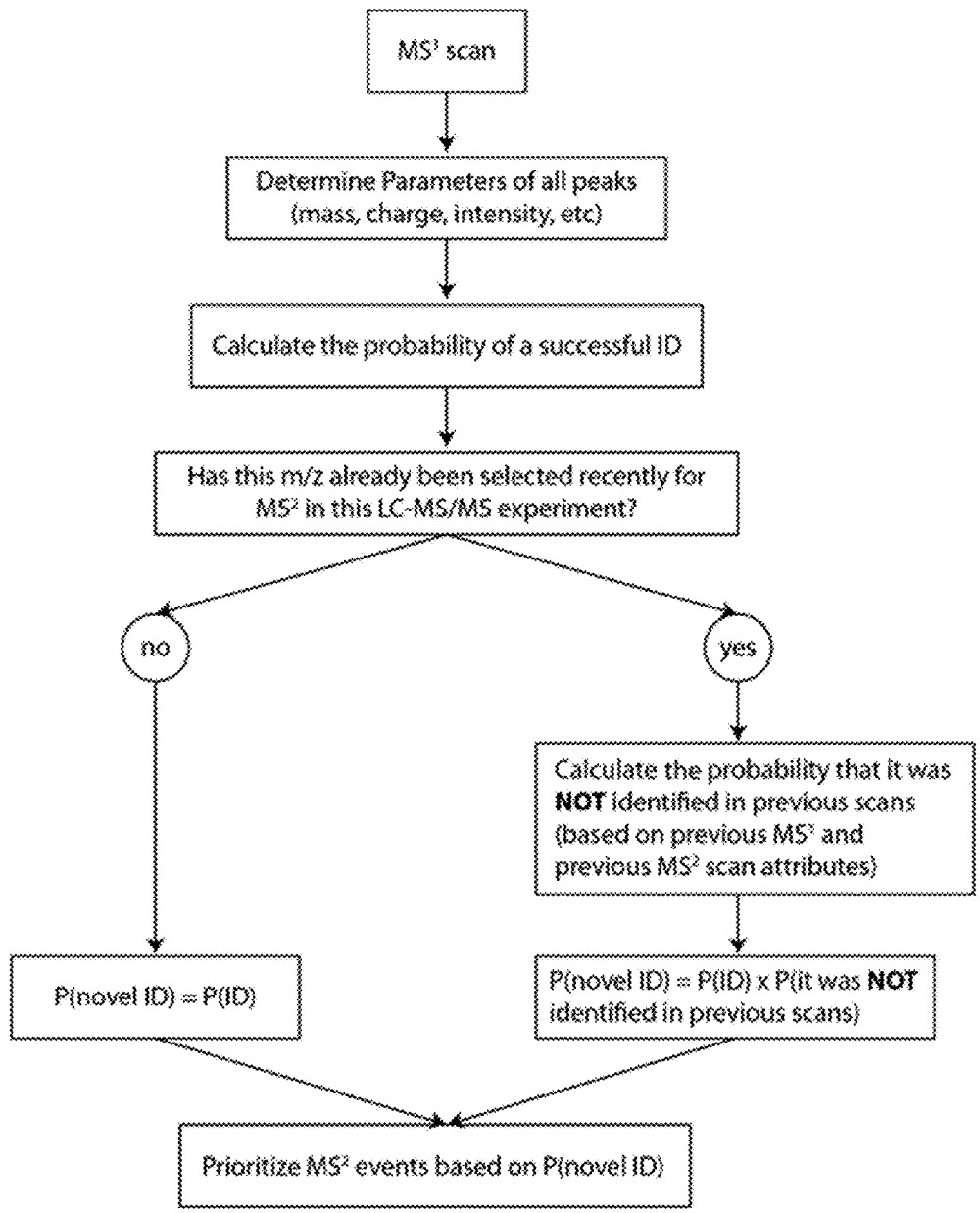
FIG. 6 provides a flow chart showing steps used to determine the probability that a MS/MS scan will result in the successful novel identification of a compound.

If it is determined that the precursor ion of interest has not been previously selected for MS/MS analysis, then the probability of the current MS/MS scan resulting in a novel identification will be the same as the calculated probability of there being a successful identification (illustrated in FIG. 6 as "P(novel ID)=P(of ID)"). However, if the precursor ion was previously selected for MS/MS analysis, then the probability of a novel identification will be the calculated probability of there being a successful identification multiplied by the calculated probability that the precursor ion was not previously identified (illustrated in FIG. 6 as "P(novel ID)=P(of ID)×P(it was not identified in previous scans)").

This method of emphasizing novel identifications is designed specifically to increase unique peptide identifications. It also obviates the need to implement dynamic exclusion systems. The prioritization of $MS^2$ events is based purely on the probability that this scan will result in a novel identification. Preliminary experiments have shown small increases in novel identifications and suggest this method could have great potential to influence the way future LC-MS/MS experiments are performed.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional peptides, chemically modified peptides, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

The invention claimed is:

1. A method of analyzing an analyte using tandem mass spectrometry, the method comprising:
   (a) providing an analyte;
   (b) generating a distribution of precursor ions from the analyte;
   (c) analyzing two or more precursor attributes of at least a portion of the distribution of precursor ions, and using said precursor attributes to calculate probabilities of identification for at least a portion of the precursor ions;
   (d) prioritizing said precursor ions according to which precursor ions have a greater calculated probability of identification, thereby generating a set of prioritized precursor ions;
   (e) fragmenting one or more prioritized precursor ions and generating a distribution of fragment ions; and
   (f) measuring one or more attributes of at least a portion of the distribution of the fragment ions, thereby generating product ion mass spectrometry data.

2. The method of claim 1 wherein said analyte is a mixture of proteins, peptides and combinations thereof.

3. The method of claim 1 wherein an algorithm is used to calculate the probability of identification for one or more of the precursor ions.

4. The method of claim 1 wherein the probability of identification for one or more of the precursor ions is calculated using generalized linear models, decisions trees, or support vector machines.

5. The method of claim 1 wherein prioritized precursor ions having higher calculated probability of identification are fragmented, and precursor ions having lower calculated probability of identification are excluded from further analysis.

6. The method of claim 1 wherein increased detection or analyzing resources are assigned to fragmented precursor ions having higher calculated probability of identification.

7. The method of claim 1 wherein said two or more precursor attributes are selected from the group consisting of mass, signal intensity, mass-to-charge ratio, charge state, signal to noise ratio, composition, and presence or absence of other precursor ions with a similar mass-to-charge ratio.

8. The methods of claim 1 wherein said one or more fragment ion attributes are selected from the group consisting of mass, signal intensity, mass-to-charge ratio, charge state, signal to noise ratio, composition, and presence or absence of other precursor ions with a similar mass-to-charge ratio.

9. The method of claim 1 wherein the analyzing, prioritizing and fragmenting steps are performed in real-time.

10. The method of claim 1 further comprising the steps of:
    performing mass spectroscopy on a training sample, thereby generating data values for a plurality of training attributes; and
    selecting two or more training attributes corresponding to said training sample, wherein said selected training attributes have data values corresponding to a higher probability of identification for said training sample than unselected training attributes;
    wherein the analyzed precursor attributes used to calculate the probabilities of identification correspond to the selected training attributes.

11. The method of claim 10 wherein said training sample is a yeast lysate or a human tryptic digest.

12. The method of claim 10 wherein said training attributes are selected from the group consisting of mass, signal intensity, mass-to-charge ratio, charge state, signal to noise ratio, composition, and presence or absence of other precursor ions with a similar mass-to-charge ratio.

13. A method of analyzing an analyte using tandem mass spectrometry, the method comprising:
    (a) providing an analyte;
    (b) generating a distribution of precursor ions from the analyte;
    (c) analyzing two or more precursor attributes of at least a portion of the distribution of precursor ions, and using said precursor attributes to calculate probabilities of identification for one or more precursor ions;
    (d) determining whether the one or more precursor ions have been previously selected for mass spectrometry analysis, and calculating the probabilities that the one or more precursor ions have not been identified in previous mass spectrometry analysis;

(e) using the calculated probabilities of identification and the calculated probabilities that the one or more precursor ions have not been identified in previous mass spectrometry analysis to generate probabilities of novel identification for the one or more precursor ions;

(f) prioritizing the one or more precursor ions according to which precursor ions have a greater probability of novel identification, thereby generating a set of prioritized precursor ions;

(e) fragmenting one or more prioritized precursor ions and generating a distribution of fragment ions; and (f) measuring one or more attributes of at least a portion of the distribution of the fragment ions, thereby generating product ion mass spectrometry data.

14. The method of claim 13 wherein said analyte is a mixture of proteins, peptides and combinations thereof.

15. The method of claim 13 wherein an algorithm is used to calculate the probability of identification, the probability that the one or more precursor ions have not been identified in previous mass spectrometry analysis, the probability of novel identification, or combinations thereof.

16. The method of claim 13 wherein the probability of identification, the probability that the one or more precursor ions have not been identified in previous mass spectrometry analysis, the probability of novel identification, or combinations thereof, are calculated using generalized linear models, decisions trees, or support vector machines.

17. The method of claim 13 wherein prioritized precursor ions having higher probability of novel identification are fragmented, and precursor ions having lower probability of novel identification are excluded from further analysis.

18. The method of claim 13 wherein increased detection or analyzing resources are assigned to fragmented precursor ions having higher probability of novel identification.

19. The method of claim 13 wherein said two or more precursor attributes are selected from the group consisting of mass, signal intensity, mass-to-charge ratio, charge state, signal to noise ratio, composition, and presence or absence of other precursor ions with a similar mass-to-charge ratio.

20. The methods of claim 13 wherein said one or more fragment ion attributes are selected from the group consisting of mass, signal intensity, mass-to-charge ratio, charge state, signal to noise ratio, composition, and presence or absence of other precursor ions with a similar mass-to-charge ratio.

21. The method of claim 13 wherein the analyzing, prioritizing and fragmenting steps are performed in real-time.

22. The method of claim 13 further comprising:
performing mass spectroscopy analysis on a training sample, thereby generating data values for a plurality of training attributes; and
selecting two or more training attributes corresponding to said training sample, wherein said selected training attributes have data values corresponding to a higher probability of identification for said training sample than unselected training attributes;
wherein the two or more precursor attributes in step (c) correspond to the selected training attributes.

23. The method of claim 22 wherein said training attributes are selected from the group consisting of mass, signal intensity, mass-to-charge ratio, charge state, signal to noise ratio, composition, and presence or absence of other precursor ions with a similar mass-to-charge ratio.

24. A tandem mass spectrometer system for analyzing an analyte, the system comprising:
a) an ion source for generating ions from the analyte;
b) first ion separation optics in communication with the ion source for separating ions according to their mass-to-charge ratios;
c) a first ion detector in communication with the first ion separation optics for detecting ions separated according to their mass-to-charge ratios;
d) ion fragmentation optics in communication with the first ion separation optics for generating fragment ions;
e) second ion separation optics in communication with the ion fragmentation optics for separating ions according to their mass-to-charge ratios;
f) a second ion detector in communication with the second ion separation optics for detecting ions separated according to their mass-to-charge ratios; and
g) a controller operably connected to the first and second ion separation optics, the first and second ion detectors, and the ion fragmentation optics,
wherein the controller controls the ion optics and detectors so as to:
(i) generate a distribution of precursor ions from the analyte;
(ii) analyze two or more precursor attributes of at least a portion of the distribution of precursor ions, wherein the two or more precursor attributes are used to calculate probabilities of identification for at least a portion of the precursor ions;
(iii) prioritize the precursor ions according to which precursor ions have a greater calculated probability of identification or a greater probability of novel identification, thereby generating a set of prioritized precursor ions;
(iv) fragment one or more prioritized precursor ions, thereby generating a distribution of fragment ions; and
(v) measure one or more attributes of at least a portion of the distribution of the fragment ions, thereby generating product ion mass spectrometry data.

25. The tandem mass spectrometer system of claim 24 wherein said controller is further able to record a plurality of mass spectroscopy attributes of a training sample, evaluate which training sample attributes correlate to increased successful identification, and select two or more precursor ion attributes which correspond to training attributes correlate to increased successful identification.

26. The tandem mass spectrometer system of claim 24 wherein the controller is able to perform steps (i)-(v) in real time.

* * * * *

UNITED STATES PATENT AND TRADEMARK OFFICE
CERTIFICATE OF CORRECTION

| | | |
|---|---|---|
| PATENT NO. | : 8,530,831 B1 | Page 1 of 1 |
| APPLICATION NO. | : 13/418972 | |
| DATED | : September 10, 2013 | |
| INVENTOR(S) | : Coon et al. | |

It is certified that error appears in the above-identified patent and that said Letters Patent is hereby corrected as shown below:

On the Title Page, Item [54] and in the Specification, Column 1, please delete the title "Probability-Based Mass Spectrometry Data Acquisition Method" and replace with --Probability-Based Mass Spectrometry Data Acquisition Method for Increased Peptide and Protein Identifications--.

Signed and Sealed this
Fifteenth Day of April, 2014

Michelle K. Lee
*Deputy Director of the United States Patent and Trademark Office*